United States Patent
Kuiken et al.

(10) Patent No.: US 10,369,028 B2
(45) Date of Patent: Aug. 6, 2019

(54) SAFETY OVERLOAD FOR DIRECT SKELETAL ATTACHMENT

(71) Applicant: Rehabilitation Institute of Chicago, Chicago, IL (US)

(72) Inventors: Todd Kuiken, Oak Park, IL (US); Michael Peshkin, Evanston, IL (US); Kyle Kaveny, Chicago, IL (US); Maxwell Keith Shepherd, Chicago, IL (US)

(73) Assignee: Rehabilitation Institute of Chicago, Chicago, IL (US)

(*) Notice: Subject to any disclaimer, the term of this patent is extended or adjusted under 35 U.S.C. 154(b) by 0 days.

(21) Appl. No.: 15/495,923

(22) Filed: Apr. 24, 2017

(65) Prior Publication Data

US 2017/0304086 A1    Oct. 26, 2017

Related U.S. Application Data (60) Provisional application No. 62/326,418, filed on Apr. 22, 2016.

(51) Int. Cl.
*A61F 2/50* (2006.01)
*A61F 2/78* (2006.01)

(52) U.S. Cl.
CPC ........ *A61F 2/78* (2013.01); *A61F 2002/5003* (2013.01); *A61F 2002/5073* (2013.01);
(Continued)

(58) Field of Classification Search
CPC ...... A61F 2/2814; A61F 2/30749; A61F 2/76; A61F 2/78; A61F 2002/7635; A61F 2002/7875; A61F 2002/7887; F16B 2/10; F16B 2/185; F16L 33/12; F16L 23/06; Y10T 403/3961; Y10T 403/4611; Y10T 403/4628; Y10T 403/4674; Y10T 403/4688; Y10T 403/648; Y10T 403/7062; Y10T 403/7064; Y10T 403/7066;
(Continued)

(56) References Cited

U.S. PATENT DOCUMENTS

| | | | |
|---|---|---|---|
| 3,157,932 A | * | 11/1964 | Kyrias .................... F16L 33/12 24/271 |
| 3,947,897 A | | 4/1976 | Owens |

(Continued)

OTHER PUBLICATIONS

Hull et al. Electromechanical Ski Release Binding With Mechanical Backup, Mar. 1997, vol. 119, pp. 145-148.
(Continued)

*Primary Examiner* — Christie L Bahena
(74) *Attorney, Agent, or Firm* — McAndrews, Held & Malloy, Ltd.

(57) ABSTRACT

Systems and methods are disclosed for prosthetic devices. In one embodiment, an apparatus comprises a first section attachable to an abutment screw of a percutaneous implant; a second section attachable to a prosthetic limb; a latch for coupling the first section with the second section, the latch releasable in response to an overload on the prosthetic limb. A compliance component may be positioned between the first section and the second section, such that when the latch releases in response to the overload, the compliance component provides a tension between the first section and the second section.

19 Claims, 7 Drawing Sheets

(52) U.S. Cl.
CPC .............. *A61F 2002/5083* (2013.01); *A61F 2002/7887* (2013.01)

(58) Field of Classification Search
CPC ......... Y10T 403/6067; Y10T 403/7069; Y10T 403/53; Y10T 403/535; Y10T 403/7071; Y10T 403/1418; Y10T 403/1454
See application file for complete search history.

(56) References Cited

U.S. PATENT DOCUMENTS

| | | | |
|---|---|---|---|
| 4,771,255 A * | 9/1988 | Shull | H01F 7/124 335/169 |
| 8,246,693 B2 | 8/2012 | Bachus et al. | |
| 2005/0234564 A1 | 10/2005 | Fink et al. | |
| 2008/0161938 A1 * | 7/2008 | Gramnas | A61F 2/60 623/33 |
| 2008/0288087 A1 | 11/2008 | Bachus et al. | |
| 2011/0136376 A1 * | 6/2011 | Johnson | A61F 2/76 439/529 |
| 2011/0190907 A1 * | 8/2011 | Porter | A61F 2/78 623/32 |
| 2012/0310371 A1 | 12/2012 | Bachus et al. | |
| 2012/0316657 A1 | 12/2012 | Bachus et al. | |
| 2013/0195540 A1 * | 8/2013 | Wozencroft | A61F 2/78 403/83 |
| 2014/0081422 A1 | 3/2014 | Hugate | |
| 2014/0156022 A1 | 6/2014 | Holt et al. | |
| 2015/0257904 A1 * | 9/2015 | Branemark | A61F 2/78 623/32 |
| 2018/0185174 A1 * | 7/2018 | Porter | A61F 2/78 |

OTHER PUBLICATIONS

Neptune et al. A New Electromechanical Ski Binding With Release Sensitivity to Torsion and Bending Moments Transmitted by the Leg, Int'l Journal of Sport Biomechanics, 1992, 8, pp. 331-349.

* cited by examiner

FIG. 11

SAFETY OVERLOAD FOR DIRECT SKELETAL ATTACHMENT

RELATED APPLICATIONS

This application claims benefit to U.S. Provisional Patent Application 62/326,418 filed on Apr. 22, 2017, which is incorporated by reference.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Amputation is the surgical removal of part or all of a limb to address trauma, tumor, disease, and congenital defects. The surgeon must find a balance between two main goals: removal of the diseased or damaged portion of the limb, and reconstruction of the remaining, or residual, limb to promote healing and maintain functionality of the limb. Amputation of the lower limb is the most prevalent major amputation surgery. As of 2005, there were 623,000 Americans living with lower limb amputations, either above or below knee. Most lower limb amputations are a consequence of disease; however, trauma and cancer are significant etiologies and account for 19% of the population.

Transfemoral amputees have amputations above their knee, which means that the knee is amputated as well as parts of the leg below the knee. A basic principle of amputation is conservation of the residual limb. When a transfemoral patient is a candidate for a prosthesis, the level of amputation is determined based on a number of factors, including prosthesis attachment and fitting, and maintaining the functional ability of the patient. As a general rule, the higher the level of transfemoral amputation, the less satisfactory the functional outcome with a prosthesis because the patient loses musculature to control the femur. Furthermore, the length of the residual limb has a significant effect on gait. Transfemoral amputees walk at reduced speeds at least 30% slower than those without amputation.

For lower limb amputees, conventional prostheses attach using a socket that suspends the prosthesis from the residual limb using negative pressure, or suction. Though this is a standard care option, many drawbacks exist, including skin-related issues (e.g., blisters, cysts, skin irritation), and compromised control of the prosthesis. The volume of a limb fluctuates throughout the day and can necessitate the removal or addition of a cloth layer, or sock, over the limb to compensate. Moreover, weight changes throughout the year can necessitate a socket revision.

Direct skeletal attachment, which can involve anchoring to the bone, is an alternative method for prosthetic attachment. Direct Skeletal Attachment (DSA) is the connection of a prosthesis directly to the bone of a residual limb. Attaching directly to the bone has both benefits and risks associated with the procedure. Attaching to the skeletal system eliminates the use of a socket. In doing so, DSA avoids skin related socket complications, allows easier donning and doffing of the prosthesis, provides greater comfort while seated, and limb volumetric change is no longer an issue. Additionally, patients have improved proprioception and sensory feedback through their residual limb, referred to as "osseoperception". Moreover, DSA can eliminate expenses associated with sockets. Despite numerous advantages of the procedure, challenges still remain. These challenges include infection, bone loss, bone fractures, loosening of hardware, and breakage of percutaneous parts. In some cases, revision surgeries may be required. The stiffness of a titanium implant is much higher than that of the surrounding compact bone, so there is a potential for bone fracture near the osteotomy due to a high external load (e.g., a fall scenario). The area above the implant is most susceptible to fracture, and there is also a risk of longitudinal bone fracture along the length of the implant. One finite element study found that bone failure was three times more likely to occur with a DSA implant than in an intact femur. In a separate numerical simulation study of DSA implants, the safety factor against bone failure was relatively low, even for level-ground walking Osseointegration, a type of DSA, refers to a direct structural and functional connection between ordered, living bone and the surface of a load-carrying implant. An implant is regarded as osseointegrated when there is essentially no relative movement at the site where the implant contacts the bone. This phenomenon is possible with a titanium implant because the bone tightly adheres to the titanium oxide surface layer of the implant instead of a layer of connective tissue forming between the bone and implant. This structural organization implies that the implant does not induce any inflammatory response. Amputees who benefit most from osseointegration can be those who are unable to tolerate a socket prosthesis, have short residual limbs, or are bilateral transfemoral amputees.

The OPRA protocol (Osseointegrated Prostheses for the Rehabilitation of Amputees) is a transfemoral osseointegration implant system. The OPRA protocol involves a two-stage surgical operation and consists of three components: the fixture, the abutment, and the abutment screw. In the first stage, the medullary cavity of the femur is hand drilled (to minimize bone heating) and a threaded self-tapping titanium fixture is screwed into the cavity. To provide ample time for osseointegration, the second surgery is performed six months later and consists of attaching a percutaneous component, the abutment, to the fixture using the abutment screw. The second procedure is followed by 6-12 months of rehabilitation during which the abutment is progressively loaded and the patient learns to recognize the pain when the implant system is overloaded.

BRIEF SUMMARY OF THE INVENTION

In an embodiment, an apparatus comprises a first section attachable to a skeletal attachment; a second section attachable to a prosthetic limb; a latch for coupling the first section with the second section, the latch releasable in response to an overload on the prosthetic limb; and a compliance component positioned between the first section and the second section, such that when the latch releases in response to the overload, the compliance component provides a tension between the first section and the second section. The skeletal attachment may be an abutment screw of a percutaneous implant.

DETAILED DESCRIPTION OF THE INVENTION

An embodiment discloses a safety mechanism, referred to herein as an "overload device" or simply as a "device", to be used with artificial limbs that attach directly to the skeletal system. The overload device may be used to assist persons with transfemoral amputation. One benefit of embodiments disclosed herein is improve the safety of bone-anchored prostheses for individuals with transfemoral amputations.

Figure 1:
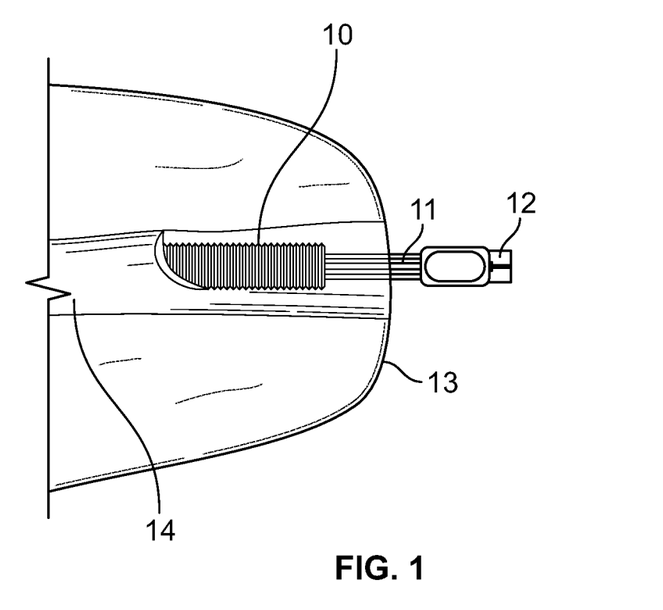
FIG. 1 displays a section view of a direct skeletal attachment.

FIG. 1 shows a view of an osseointegrated implant system, comprising fixture 10, abutment 11, abutment screw 12, skin 13, and bone 14. In various embodiments, systems and methods are disclosed that can prevent overloading of the bone and implant for prostheses that are attached directly to the skeletal system. In an embodiment, such systems and methods may be used in connection with an OPRA implant system, which it is a threaded implant that is potentially susceptible to torsion and loosening.

In an embodiment, an overload device functions as a fail-safe mechanism to protect an osseointegrated implant system and bone from overloading. The overload device may function as a rigid coupler between an abutment and a prosthesis during normal activity, or activities of daily living (ADLs). During overload, the overload device may change compliance to protect the user. One embodiment comprises a ball and socket held together by a clamp that can be quickly released, for example, as shown in FIG. 2A.

Figure 2A:
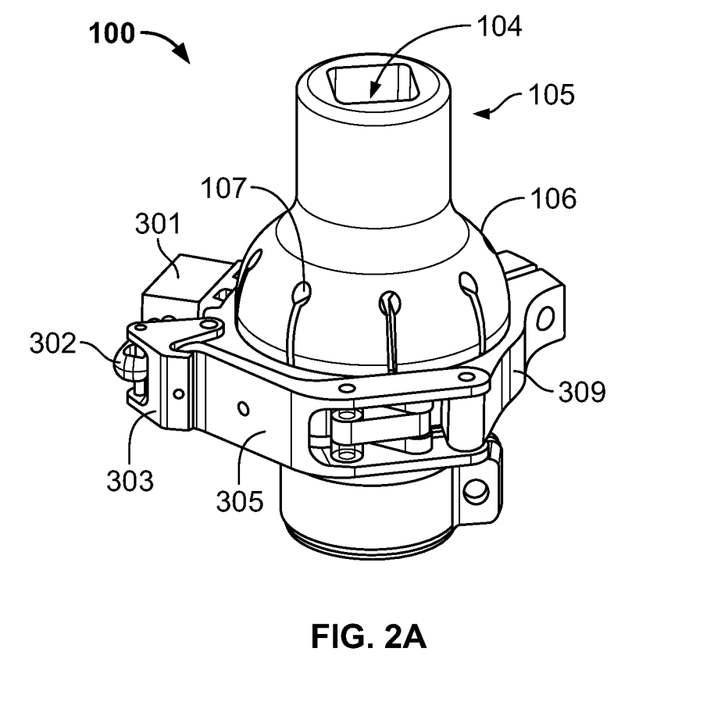
FIG. 2A displays a perspective view of an embodiment of an overload device.

FIG. 2A displays a perspective view of the overload device 100. A socket 105 has abutment opening 104 to receive the abutment 12 osseointegrated into a patient limb. The socket 105 has a socket face 106 that surrounds the exterior of the top portion of the device 100. A ball 112 (shown in FIG. 5) is positioned in the interior of the socket 105. The socket face 106 is circumscribed by a clamp 309. When the clamp 109 is closed, the socket face 106 pushes into the outer surface of the ball 112, providing a force on the ball 112 that keeps it in position. The socket face 105 may have one or more slits 107 which improves the ability of the socket 105 to be closed by the clamp 309.

Figure 2B:
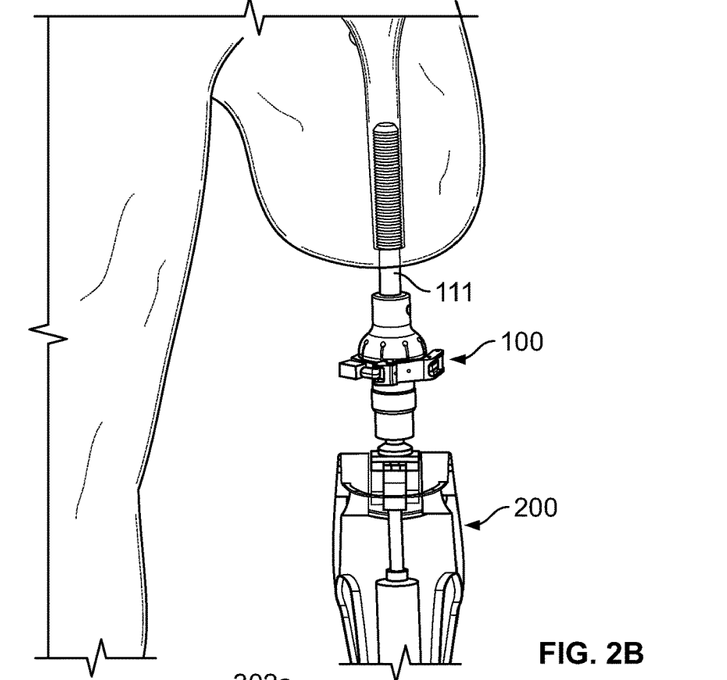
FIG. 2B displays an elevation view of an embodiment of an overload device.

The overload device 100 further comprises a solenoid 301 attached to a linkage comprising link 302 and link 303. Link 303 clasps a latch 305. The linking and latching aspects are disclosed in further detail with respect to FIG. 3. FIG. 2B shows an embodiment of the device connecting a patient's residual limb to a prosthetic arm. Specifically, FIG. 2B displays a front view of the device 100 connecting an osseointegrated system comprising abutment 11 with a prosthesis 200. As shown in FIG. 2b, the device 100 is positioned between the abutment 11 and the prosthesis 200. When the device 100 is triggered, the device 100 becomes compliant to avoid injury to the prosthesis 200 as well as to the individual using the osseointergated system.

Figure 4:
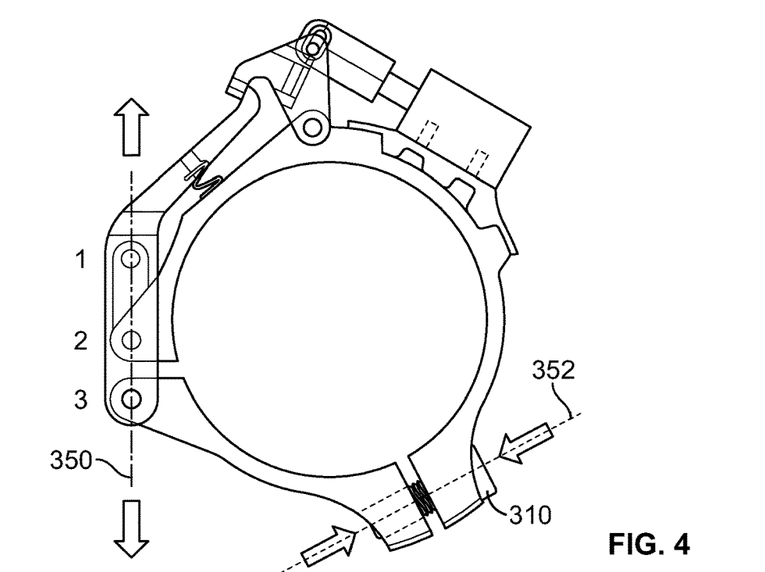
FIG. 4 displays another plan view of an embodiment of a clasp system for an overload device.

The ability to release quickly is one feature of various embodiments. A quick release allows the overload device to divert an overload force from being transferred from the prosthesis to the implant system or bone. For example, the overload device may store energy from the clamping force of a screw in a mechanical singularity, for instance as shown in FIG. 4. As the screw is tightened, hoop stresses develop along the circular ring of the clamp, which want to separate the two pieces of the ring. When the three shear pin holes are aligned the forces at the holes are also aligned. This enables the clamp to remain closed without applying any force at the latch (other than the force from the spring).

Figure 3:
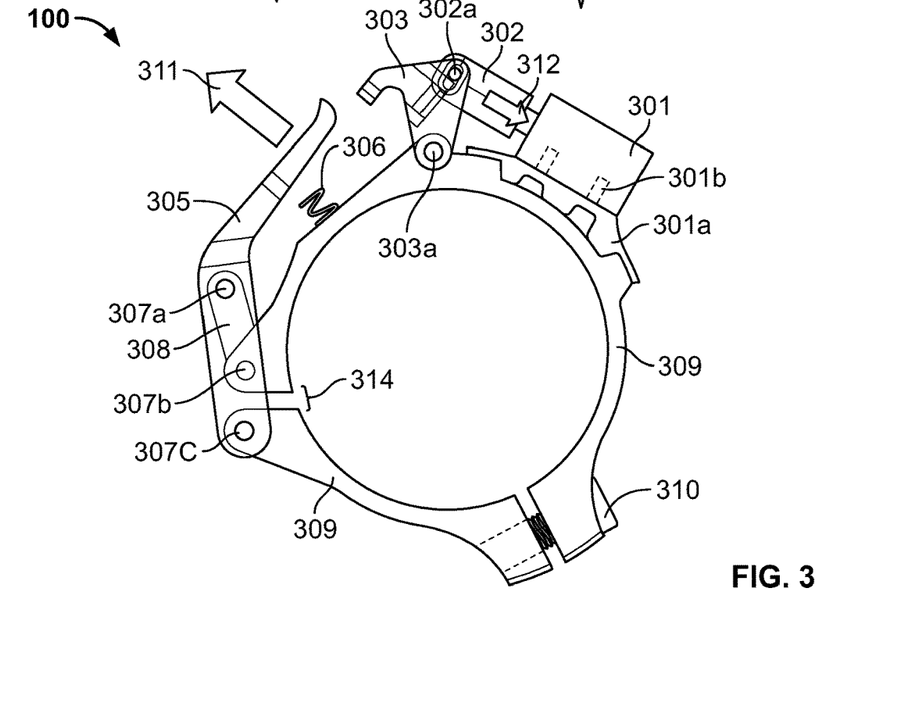
FIG. 3 displays a plan view of an embodiment of a clasp system for an overload device.

FIG. 3 displays a top view of the device 100, showing certain of those elements involved in the triggering of the device 100. In the embodiment shown in FIG. 3, a solenoid 301 is attached by attachment 301a and attachment 301b to the clamp 309. The solenoid 301 is connected to link 302. When the solenoid 301 fires, it draws link 302 towards it in the direction indicated by arrow 312. Link 302 is connected to link 303 by linkage 302a. Link 302 pulls on link 303, causing link 303 to pivot around pin 303a. Link 303 has a clasp at its outer end which claps to the flanged end of latch 305, as shown in FIG. 3. When link 303 pivots away from the latch 305, the latch 305 disengages from the link 303. Further, a spring 306 may be positioned to push latch 305 out of an engaged position. As the latch 305 disengages, moving in the direction of arrow 311, the pins 307a, 307b, and 307c are moved out of their singularity position (link 308 pivoting between pin 307a and 307b as shown in FIG. 3). This movement creates a gap 314 between the portions of the clamp 309, which loosens the socket face 106, thus loosening the position of the ball 112.

Figure 5:
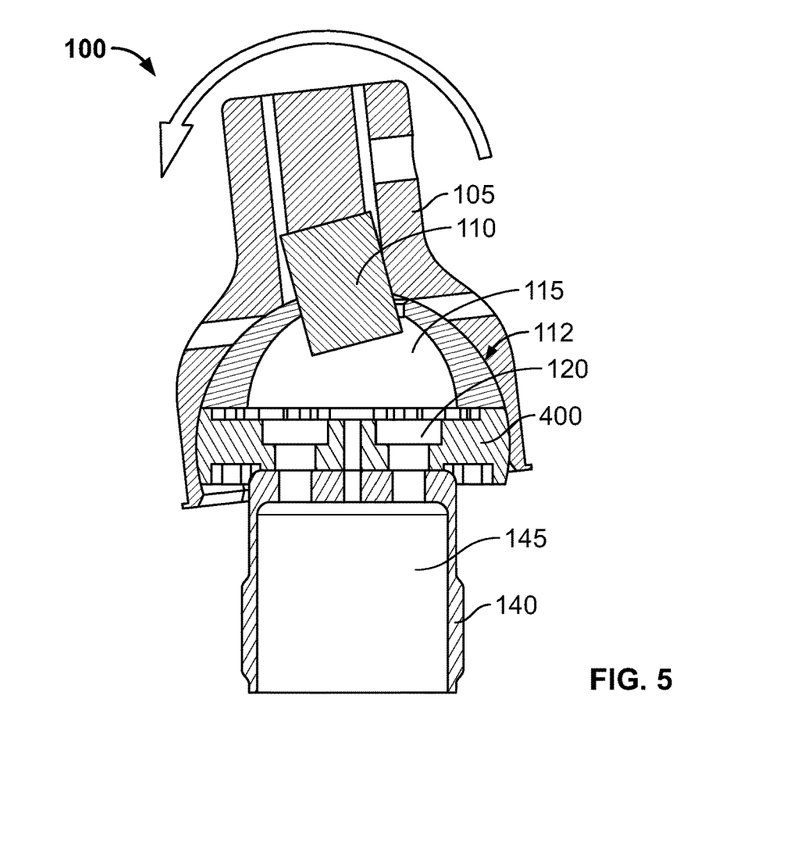
FIG. 5 displays a section view of an embodiment of an overload device.

One advantage of using a singularity to store the energy from the screw is that the stored energy can be released instantaneously, for example as shown in FIG. 3. The stored energy is released when the solenoid pulls the latch open and the spring pushes the lever out of the singularity position. Instead of detaching the prosthesis during an overload, like a ski from a ski boot during a fall, a rubber bumper is engaged which absorbs a portion of the overload force, as shown for example in FIG. 5. A bumper 110 is partially positioned in the interior of the socket 105 and also partially positioned within an opening of the puck cap 115 positioned interior to the ball 112. The upper portion of the system is connected to the lower portion via attachment 120, which connects into pylon clamp 140 and pylon 145. As shown in FIG. 5, the bumper 110 is engaged to absorb a portion of the overload force. Specifically, friction holds the bumper 110 between the interior opening of the socket 105 and the upper portion of the ball 12. In this way, the bumper 110 provides a tension between the socket 105 and the second upper portion of the ball 112 while also providing compliance between the two portions.

The abutment can serve as an attachment site for a prosthetic arm or leg or other assistive device and provides a direct connection to the bone. The abutment helps avoid torsion along the long axis of the bone, which can cause loosening of the implant or fractures. For example, a mechanical fuse may be developed that complies before an overload force can be transferred to the bone or abutment.

Figure 6:
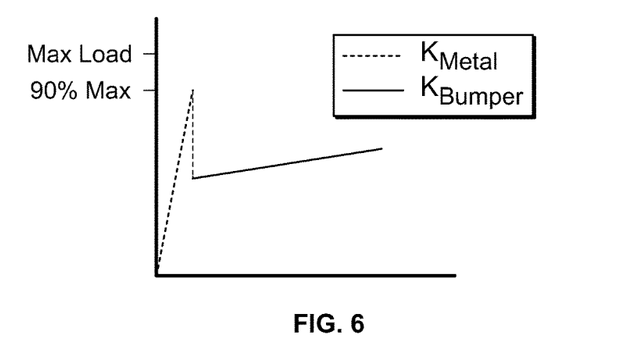
FIG. 6 displays a plot of stiffness.

By engaging the bumper, the compliance of the device changes from the stiffness of the material of the device, such as mild steel, to the stiffness of the rubber bumper, for example as shown in FIG. 6. This feature prevents the ball from sliding out of the socket and, will allow the user to maintain balance on the prosthesis after the device is released (i.e., becomes unclamped). This can be particularly useful in the case of a trip recovery (i.e., recovering one's balance after a trip), but other applications are also contemplated. The bumper can allow the user to maintain balance with the prosthesis after the device releases if overload occurs during a recovery response. In various embodiments, the bumper prevents the device from detaching during overload.

In an embodiment, the device 100 detects overload with a custom-designed three degree-of-freedom (DOF) load cell sensor, using 12 strain gauges, and a microcontroller. The microcontroller may be a PIC32MX795F512L (Microchip Technology Inc., Chandler, Ariz.), or another suitable microcontroller. The software embedded on the PIC32 microcontroller works by scanning 3 channels sequentially at 100 kilosamples per second (once every 10 microseconds). Other embodiments may include simultaneous channel scanning and additional input channels.

The custom load cell detects moments about all three axes, and has the capacity for additional gauges for six DOFs. The custom load cell (shown in FIG. 7) may be integrated within the ball section to record loads applied to the device. The load is converted to analog voltage and is read by the microcontroller. The microcontroller may be programmed with a release threshold that can be changed and individualized based on the weight of the user and point in the user's post-surgical rehabilitation program. In the case of an overload, the release threshold is exceeded and the microcontroller sends a digital voltage to signal the solenoid to open, as shown in FIG. 3. For example, once a sample is recognized outside of a predefined range (this range represents the activation loads) voltage is sent to the solenoid to trigger the release of the mechanism. The solenoid pulls on a latch and releases a lever from its singularity position. The device is now in an open state and the overload is diverted away from the implant system and bone.

The ZonHen solenoid was able to produce a maximum force of 3.05 N. The solenoid was able to trigger the latch to release at tightening torques of 6 and 7 Nm. A tightening torque of 7 Nm produced the necessary holding moments in bending and torsion to withstand the activities of daily living. In an embodiment, the solenoid may be encased to prevent non-actuated releases due to bumping the latch or solenoid plunger. The forces required to release the latch may range from 2.6-6.7 N for tightening torques of 6-8 Nm. The observed release force may be variable, but can be minimized by setting the lever in an over-center position (i.e. at a singularity) and by reducing the friction between the latch and lever by using strips of Teflon film. The variability of this friction can be removed, for instance, by using a needle-roller bearing on the latch.

In the embodiment shown in FIG. 4, mechanical singularity is achieved when the three shear pin holes, labeled 1-3, are aligned. In this embodiment, there is no force applied to the latch except for the spring. The arrows represent the line 350 of actions of the forces. The dashed circle represents the outline of the socket.

As shown in FIG. 3, the solenoid pulls the latch open and the lever is released. The spring ensures that the lever does not remain in a singularity position after the latch is opened. The arrows represent the line of actions of the forces. The dashed circle represents the outline of the socket.

The device can function as a fail-safe mechanism to protect an osseointegrated implant system and bone from overloading. The device can function as a rigid coupler between an abutment and a prosthesis during normal activity, or activities of daily living (ADLs). During overload, the device changes compliance to protect the user. In an embodiment, the device comprises a ball and socket held together by a clamp that can be quickly released, for example as shown in FIG. 2. The ability to release quickly is critical in certain circumstances, certain applications, and certain embodiments, because this allows the device to divert an overload force from being transferred from the prosthesis to the implant system or bone. To accomplish this task, the device stores the energy from the clamping force of a screw 310 in a mechanical singularity (FIG. 4). As the screw 310 is tightened, hoop stresses develop along the circular ring of the clamp, which want to separate the two pieces of the ring. When the three shear pin holes are aligned the forces at the holes are also aligned. This enables the clamp to remain closed without applying any force at the latch (other than the force from the spring). One advantage of using a singularity to store the energy from the screw is that the stored energy can be released instantaneously, for instance as shown in FIG. 3. The stored energy is released when the solenoid pulls the latch open and the spring pushes the lever out of the singularity position. Instead of detaching the prosthesis during an overload, like a ski from a ski boot during a fall, a rubber bumper is engaged which absorbs a portion of the overload force, for example as shown in FIG. 5. As shown in FIG. 5, after the clamp ring is released, the device is held by a rubber bumper, and the compliance of the device (in rotation) becomes the stiffness of the bumper. This feature can allow for balance recovery.

By engaging the bumper, the compliance of the device changes from the stiffness of mild steel (in the case of the mild steel prototype), to the stiffness of the rubber bumper, for instance as shown in FIG. 6. FIG. 6 displays an idealized graph of applied load vs. displacement. This graph is intended to show how the stiffness, k, of the device changes to prevent overload being transferred to the bone.

This feature can prevent the ball from sliding out of the socket and allows the user to maintain balance on the prosthesis after the device becomes unclamped. This can be useful in the case of a trip recovery (i.e., recovering one's balance after a trip). The bumper can allow the user to maintain balance with the prosthesis after the device releases if overload occurs during a recovery response. Without the bumper, the device would detach during overload. If this occurred during a recovery response, a fall and subsequent injury to the user could result.

The device can detect overload with a three degree-of-freedom (DOF) load cell sensor, using 12 strain gauges, and a microcontroller. The load cell may detect moments about all three axes, and has the capacity for additional gauges for six DOFs. The load cell, shown in FIG. 7, may be integrated within the ball section to record loads applied to the device.

Figure 7:
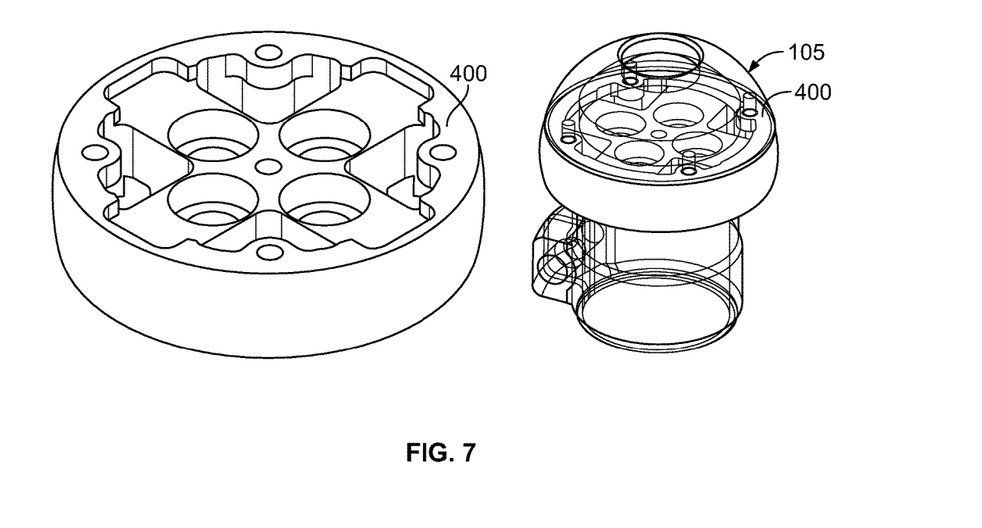
FIG. 7 displays perspective views of an exemplary load cell.
Figure 8A:
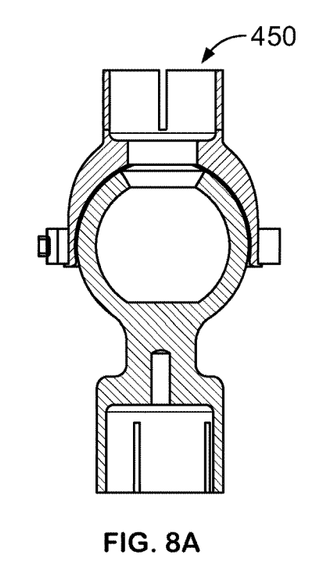
FIG. 8 displays section views of alternative embodiments of an overload device.
Figure 8B:
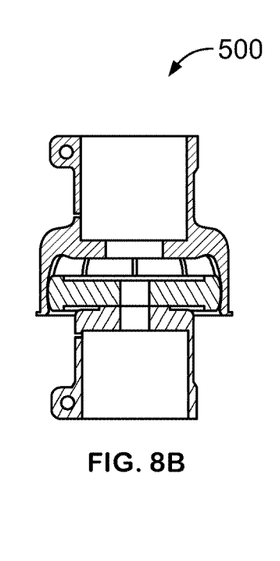
Figure 8C:
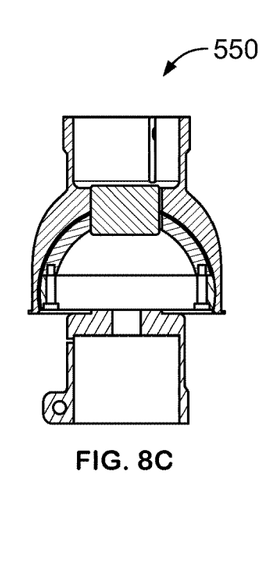
Figure 8D:
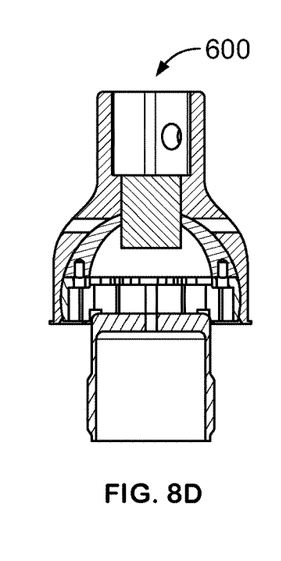
Figure 9:
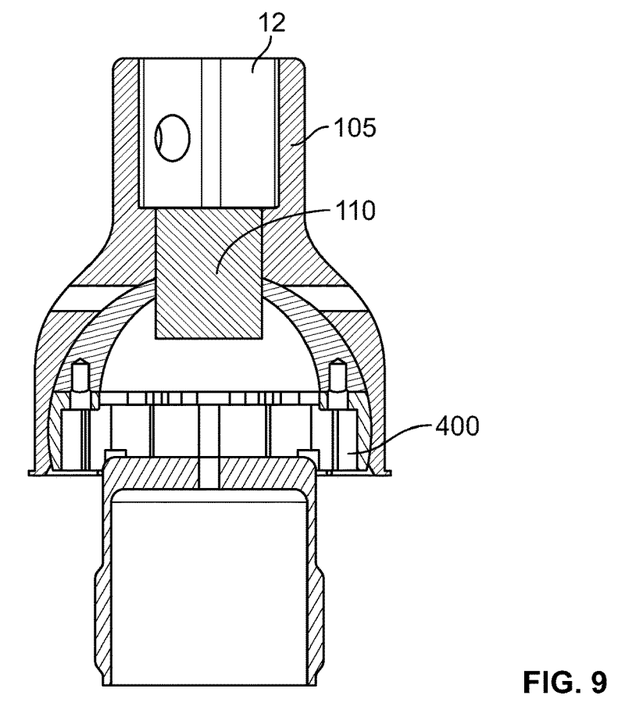
FIG. 9 displays another section view of an embodiment of an overload device.

Load cell design. As shown in FIG. 7, the load cell 400 is designed to allow up to six DOFs by attaching strain gages to the surfaces of the four cantilever arms. The load is converted to analog voltage and is read by the microcontroller. The microcontroller is programmed with a release threshold that can be changed and individualized based on the weight of the user and point in the post-surgical rehabilitation program. In the case of an overload, the release threshold is exceeded and the microcontroller sends a digital voltage to signal the solenoid to open (see FIG. 3). The solenoid pulls on a latch and releases a lever from its singularity position. The device is now in an open state and the overload is diverted away from the implant system and bone. The load cell 400 may be positioned within the overload device 100 as shown in FIG. 7 and FIG. 9.

Various embodiments are shown in FIGS. 8A, 8B, 8C, and 8D. Embodiments 450, 500, 550, and 600 may include a separate load cell (shown FIG. 8A), a load cell integrated in place of the ball (shown FIG. 8B), a hemispherical cap (shown FIG. 8C), and a rubber bumper (shown FIG. 8D), respectively. Various embodiments may be manufactured from different materials, such as mild steel or titanium alloy.

Figure 10:
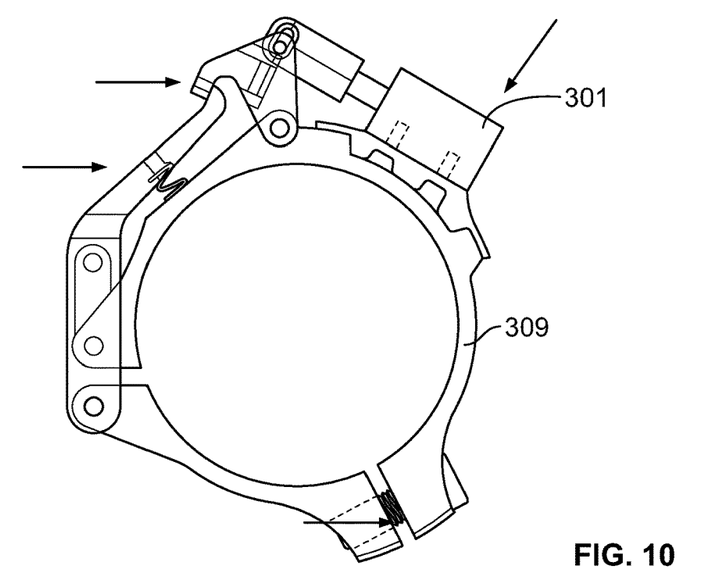
FIG. 10 displays another plan view of an embodiment of a clasp system for an overload device.

The clamp ring shown in FIG. 10 uses a mechanical singularity (for example shown in FIG. 4) to store energy while the device is clamped. The device may be released by a solenoid (ZHO-0420S-05A4.5, ZonHen Electric Appliances, Shenzhen, China) that pulls open the latch holding the lever. The lever is pushed out of the singularity, or over-center, position with the aid of a spring. Once the device is released, the ball will no longer be held rigidly within the socket.

Figure 11:
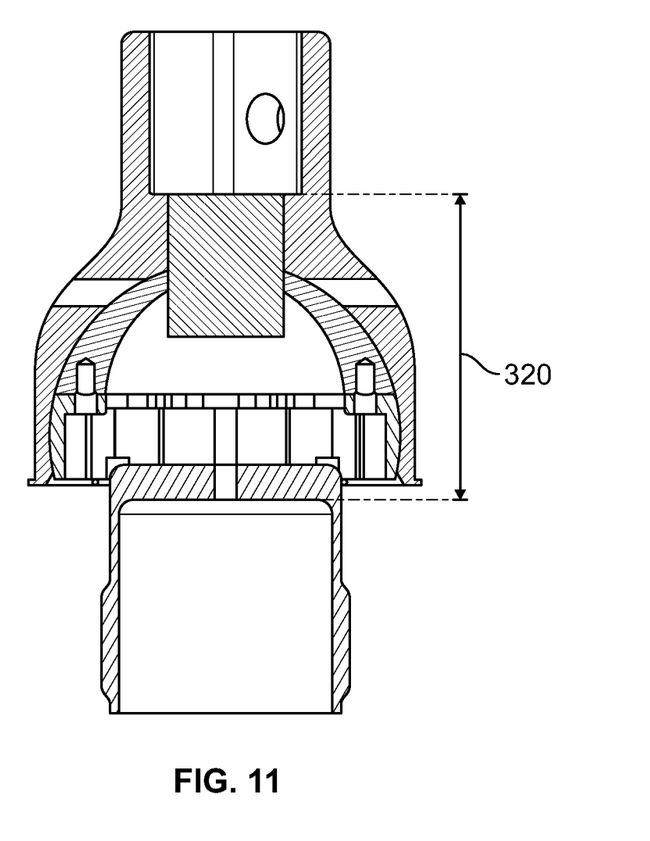
FIG. 11 displays another section view of an embodiment of an overload device.

The effective height of the device 320 (shown in FIG. 11), or the height added to the user, may be decreased by removing the original ball and replacing it with a puck. In this design, the load cell may be integrated into the puck. Also, to account for the reduced length of the socket petals, spiral cuts may be added to increase the length and flexibility of the petals. Vertical cuts may reduce manufacturing complexity and anticipated costs. The bumper may be made of polyurethane, such as 60 A durometer polyurethane (McMaster-Carr, Elmhurst, Ill.). The effective height of the device, in one embodiment, is 1.7 inches and weight is 1.6 pounds, both of which are below the targets specifications of 3 inches and 2 pounds. In an embodiment, the device may open in 16.7 milliseconds, which is below a target specification of 25 milliseconds.

The key requirements can be clinically relevant to the extent they incorporate the largest population possible. These features include effective height, weight, and threshold. Effective height (FIG. 11) is the amount of length the device adds between the residual limb and the prosthesis. This specification was selected as less than 3 inches, but must be minimized to accommodate individuals with long residual limbs. Weight is another specification to be minimized to reduce user effort. This dimension was chosen as less than 2 pounds. Lastly, the threshold specification was set to patients in the bodyweight range of 90-220 pounds. This range reflects the inclusion criteria for the OPRA protocol.

Table 1 shows certain requirements for a preferred embodiment of the device

The requirements (Table 1) are for a preferred embodiment, and other embodiments are contemplated that do not necessarily meet one or more of such requirements. There are multiple mechanical requirements that may have important considerations in order for the patient to reliably walk on an assistive device connected to the osseointegration device. The contact interface between the ball and the socket must have enough friction to withstand forces encountered during everyday activities. The holding moment represents the upper limit the device must be able to resist. The holding moment is a result of the clamp ring exerting a radial clamping force on the ball and socket, and depends on the friction at that interface. The holding moment in bending, 86.4 Nm (see Calculations 2), was chosen as the yield moment of the abutment because the device is designed to release before the abutment yields. The holding moment in bending, 86.4 Nm, represents the upper limit of the implant system and corresponds to the heaviest patient included in the protocol (100 kg). The holding moment in torsion was chosen as 60 Nm. This moment reflects approximately a third of the ultimate torsional strength (see Calculations 3) of compact bone (calculated from the shear strength of compact bone in literature) and approximately half of the yield moment in torsion for a titanium abutment (see Calculations 4). Literature values for the removal torque of an osseointegrated fixture exist; however, these values are low (less than 2 Nm), due to the small diameters of the implants (2-6 mm), and were implanted transcortically. The OPRA fixture is typically 16-20 mm in diameter and implanted intramedullary. Other values should be apparent to one skilled in the art.

Finite element analysis (FEA) may be used to verify that each part can withstand the maximum ground reaction force (GRF) from various common activities with a factor of safety of 2. Factor of safety may be calculated based on the yield strength of the material (i.e., when the material transitions to plastic, permanent deformation). A factor of safety of 2 means that the part will reach its yield strength (i.e., fail) at twice the design load. Factor of safety typically ranges from 1.3 to 5 and is selected based on the potential harm to the user, quality and consistency of materials and manufacturing, and knowledge of the actual loads and environment.

TABLE 1

| Requirement | Reason | Critical/Key | Specification |
| --- | --- | --- | --- |
| Holding moment | Must hold during everyday forces encountered | Critical | 86.4 Nm1 bending 60 Nm torsion |
| Mechanical Robustness | Must withstand weight and impact forces | Critical | >4.3 kN axial loading2 >5.6 kN radial loading |
| Latency | Must release quick enough to event overloading | Critical | <25 msec |
| Effective height | Minimal vertical height | Key | <3 in (7.62 cm) vertical length |
| Weight | Avoid unnecessary fatigue to the user | Key | <2 lbs (0.91 kg) |
| Thresholds | Adjustable to accommodate a range of patients | Key | 90 to 220 lbs (41 to 100 kg) patient bodyweight |

A factor of safety of 2 was selected to ensure adequate strength, accounting for the potential harm to the user, while minimizing the weight that the user must carry. Other values for a factor of safety may be appropriate, depending on the particular embodiment. Table 2 summarizes GRFs during different activities. For example, a single-leg land from a 30 cm box produced the highest GRF (excluding falls). In a preferred embodiment, the axial load was chosen as 4.3 kN and adding a safety factor of 2. The radial force was chosen as 5.6 kN because this is the force, applied to the ball and socket, needed to hold against the max moment.

The impact from a fall can occur over a millisecond time scale. Therefore, the latency (i.e., the delay from the onset of impact to the device release) may be verified and minimized to ensure that the device releases prior to injury. One aspect includes considering the latency in a microcontroller-based system because the delay from the microcontroller must be accounted for. A typical delay is on the order of tens of microseconds. The maximal latency was selected based on a set of data in which a transfemoral amputee with an osseointegrated prosthesis fell forward and the resultant loads were captured by a six degree-of-freedom load cell. The individual who fell experienced a moment about the medio-lateral (M-L) axis that increased to a maximum over a 55 millisecond time frame. A target of 25 milliseconds for the maximal latency was selected to account for the moment ramp up, system delay, and release before the maximum is reached.

Table 2 shows moments and Ground Reaction Forces during various activities. AP and ML are the moments about the anterior-posterior axis and medio-lateral axis, respectively. Torsion is moment about the longitudinal axis. For hip and knee moments positive is extension. Patients with transfemoral osseointegrated implants (TF OI) were fitted with a 6 degree-of-freedom load cell distal to the abutment. Common activities were separated from falls.

Table 3 indicates the results of a preferred embodiment, compared to target values for the operation of the device.

TABLE 3

| Requirement | Critical/Key | Target | Results |
|---|---|---|---|
| Holding moment | Critical | 86.4 Nm4 bending 60 Nm torsion | 108.5 Nm bending 68 Nm torsion |
| Mechanical Robustness | Critical | >4.3 kN axial loading5 >5.6 kN radial loading | All parts above a minimum safety factor of 2 with applied loads of 4.3 and 5.6 kN |
| Latency | Critical | <25 msec | 16.7 msec |
| Effective height | Key | <3 in (7.62 cm) vertical length | 1.7 in (4.3 cm) |
| Weight | Key | <2 lbs (0.91 kg) | 1.6 lbs (0.73 kg) |
| Thresholds | Key | 90 to 220 lbs (41 to 100 kg) patient body weight | 90 to 220 lbs |

The activation load or threshold of when a device releases can be changed easily (e.g., a LCD screen and buttons). Feedback can be provided to the user when an activity is nearing a threshold to warn the user that the activity is

TABLE 2

| Activity | Moment at Device (Nm) | Ground Reaction Force | Subjects | Notes |
|---|---|---|---|---|
| Walking | — | 1.1 BW | 10 | Able-bodied subjects |
| Walking | 21 (AP axis) −20 (ML axis) 5 (torsion) | 675 N (0.80 BW) | 9 | TF OI subjects |
| Up/Down Ramp | 22/25 (AP axis) −20/−30 (ML axis) 6.3/5.3 torsion) | 704 N/699 N (0.84 BW/0.83 BW) | 9 | 6.5°/−6.5° TF OI |
| Up/Down Ramp | — | 1.1 BW/1.3 BW | 11 | 10°/−10° Able-bodied |
| Up/Down Stairs | 19/18 (AP axis) —/10 (ML axis) 5.3/3.7 (torsion) | 769 N/649 N (.91 BW/.77 BW) | 9 | TF OI |
| Up/Down Stairs | — | 1.1 BW/1.5 BW | 10 | Able-bodied, 42°/−42° |
| Activities of Daily Living | −98.8 (AP axis) 60.2 (ML axis) 17.9 (torsion) | 1005 N (1.2 BW) | 1 | TF OI, Peak loads from 5 hours continuous recording |
| Land from Box (30 cm) | — | 2000 N (2.97 BW) | 18 | Able-bodied, Single-leg box land |
| Forward Fall | 10.46 (AP axis) 153.4 (ML axis) 30 (torsion) | 1210 N (1.3 BW) | 1 | TF OI, hand contact on wall reduced ground impact |
| Backward Fall from Walk | −128 ± 117 (AP axis) 90 ± 122 (ML axis) 81 ± 87 (torsion) | 1099 ± 269 (1.49 BW) | 1 | Able-bodied, leg buckled underneath body, inverse dynamics calculation to 240 mm superior to knee joint axis |
| Forward Fall from Stand | −126 ± 37 (AP axis) 88 ± 25 (ML axis) 20 ± 8 (torsion) | 2614 ± 346 (3.55 BW) | 1 | Able-bodied, landed on both knees |
| Forward Fall from Walk | −110 ± 63 (AP axis) 124 ± 47 (ML axis) 32 ± 19 (torsion) | 3274 ± 519 (4.45 BW) | 1 | Able-bodied, landed on both knees | unsafe (e.g., high impact plyometric exercises). Also, the device can be used to log data over time, which can be used for health purposes, to track the history of falls (e.g. events when device triggered), and monitor time spent wearing the prosthesis.

In an embodiment, when the device is triggered it changes compliance, rather than detaching. This stance recovery feature can enable users to recover their balance after the device has released, which can help to reduce falls and related injuries. One scenario where stance recovery is important is directly after a user trips and successfully recovers with the prosthesis. The high ground reaction force may cause the device to release, but the user can maintain balance because the bumper will keep the ball within the socket. This feature will enable the prosthesis to provide some level of support to potentially help the user avoid falling, while preventing large forces and torques from being transmitted to the bone and implant.

One consideration is the selection of the threshold of when the device releases (set within the microcontroller). If the threshold is set too low, the device will release at too low of a force, increasing the opportunities for the user to incur injuries. If the threshold is set too high, the device will not trigger when necessary and the overload forces will be transferred to the implant, potentially causing damage to the implant or bone fracture. Additionally, thresholds may be individualized for the user depending on factors such as weight and amputation level. One study noted that DSA overload safety devices protecting against bending moments should set their release limits based on the amputation height of the user.

The activation load may be set to 90% of the maximum load allowable by the abutment (77.8 kg in bending). However, this percentage may be decreased in order to provide a larger safety margin or to increase the window of time the device must release within.

In another embodiment, rather than having the device release when a load threshold is passed, the device may release in response to a particular rate of change of the load. In such an embodiment, the window in which the device must release could be lengthened, for instance to 40-45 milliseconds.

In other embodiments, a locking solenoid or a bistable solenoid may be employed. A bistable solenoid typically incorporates a permanent magnet to hold the plunger in a set position (utilizing no power). When powered, the solenoid actuates and retracts the plunger. Standard bistable solenoids are commercially available or a custom solution can be pursued (TLX Technologies, Pewaukee, Wis.).

Additionally, in certain embodiments, code of the device can include multiple conditions. For example, the device currently works by releasing when the analog-to-digital convertor (ADC) input voltage exceeds a designated window (for example, −0.3V to 3V). The ADC input from the load cell reads applied load over time. The device can also be set to release when the slope (or rate of change of the load) of the input voltage exceeds a value. The assumption is that for an impact over a given time the greater applied load, the greater the slope. Sensing the rate of change of the ADC input, or load, over time can improve the latency of the device.

In various embodiments, a redundant aspect may be introduced, to provide a backup or secondary mode of operation into the system in case a primary feature fails (e.g., the microcontroller). One example of such redundancy is to design the upper limit of the holding moment between the ball and socket to be lower than the force to bend the abutment (and much lower than the load to loosen the implant or damage the bone). The holding moment in torsion needs to be lower than in bending. This can be addressed by adding a circumferential groove in the ball (such as with a gasket) that enables a lower torsional holding moment.

What is claimed is:

1. An apparatus, comprising:
   a first section attachable to a skeletal attachment;
   a second section attachable to a prosthetic limb;
   a latch configured to rigidly couple the first section with the second section and to release the rigid coupling in response to an overload on the prosthetic limb, wherein the latch comprises a plurality of pins arranged in parallel when the latch is closed; and
   a compliance component positioned partially within an interior of the first section and partially within an interior of the second section, such that when the latch releases the rigid coupling in response to the overload, the compliance component provides a tension between the first section and the second section and prevents detachment of the first section from the second section.

2. The apparatus of claim 1, wherein the skeletal attachment is an abutment screw of a percutaneous implant.

3. The apparatus of claim 1, wherein the plurality of pins is at least three pins.

4. The apparatus of claim 1, wherein the compliance component is made of rubber.

5. The apparatus of claim 1, wherein the first section comprises a socket.

6. The apparatus of claim 5, wherein an outer face of the socket comprises a plurality of slits.

7. The apparatus of claim 1, further comprising a load cell that allows the latch to release the rigid coupling in response to an overload on the prosthetic limb.

8. The apparatus of claim 7, wherein the load cell is positioned in the first section.

9. An apparatus, comprising:
   a first section attachable to a skeletal attachment;
   a second section attachable to a prosthetic limb;
   a latch for coupling the first section with the second section, the latch releasable in response to an overload on the prosthetic limb;
   a compliance component positioned between the first section and the second section, such that when the latch releases in response to the overload, the compliance component provides a tension between the first section and the second section, wherein the latch is released using a solenoid.

10. An apparatus, comprising:
    a first section attachable to a skeletal attachment;
    a second section attachable to a prosthetic limb;
    a clamp configured to rigidly couple the first section with the second section;
    a clasp coupled to a first portion of the clamp;
    a latch configured to engage the clasp to cause the clamp to rigidly couple the first section with the second section and to disengage the clasp in response to an overload on the prosthetic limb; and
    a compliance component positioned between the first section and the second section, such that when the clasp disengages the latch in response to an overload on the prosthetic limb, the compliance component provides a tension between the first section and the second section.

11. The apparatus of claim 10 further comprising a link configured to store energy from the clamp when the latch engages the clasp and to release the energy in response to the latch disengaging the clasp.

12. The apparatus of claim 10 wherein the first section comprises a socket with a socket face and the second section has the shape of a ball.

13. The apparatus of claim 12 wherein when the clamp rigidly couples the first section with the second section, the socket face applies a force on the ball-shaped second section.

14. The apparatus of claim 10 wherein the compliance component extends between an interior of the first section and an interior of the second section.

15. The apparatus of claim 10 wherein the compliance component prevents detachment of the first section from the second section in the event of an overload on the prosthetic limb.

16. The apparatus of claim 10 wherein the latch extends about a circumference of the clamp.

17. The apparatus of claim 10 further comprising a load cell that allows the clasp to disengage the latch in response to an overload on the prosthetic limb.

18. The apparatus of claim 17 wherein the load cell monitors the amount of load applied to the apparatus and triggers a solenoid once a threshold is exceeded.

19. The apparatus of claim 18 wherein the solenoid acts on the clasp to disengage the latch once a threshold is exceeded.

* * * * *